(12) United States Patent
Gilman (10) Patent No.: US 8,460,899 B2
(45) Date of Patent: Jun. 11, 2013

(54) METHODS FOR IDENTIFYING NUCLEIC ACID LIGANDS

(75) Inventor: Vladimir Leo Gilman, Westford, MA (US)

(73) Assignee: Vivonics, Inc., Waltham, MA (US)

( * ) Notice: Subject to any disclaimer, the term of this patent is extended or adjusted under 35 U.S.C. 154(b) by 0 days.

(21) Appl. No.: 13/538,461

(22) Filed: Jun. 29, 2012

(65) Prior Publication Data

US 2012/0301890 A1    Nov. 29, 2012

Related U.S. Application Data

(63) Continuation of application No. 12/611,436, filed on Nov. 3, 2009, now Pat. No. 8,236,570.

(51) Int. Cl.
*C12P 19/34* (2006.01)
*C12Q 1/68* (2006.01)

(52) U.S. Cl.
USPC .......................................... 435/91.2; 435/6.12

(58) Field of Classification Search
None
See application file for complete search history.

(56) References Cited

U.S. PATENT DOCUMENTS

| 5,861,254 | A  | * | 1/1999  | Schneider et al. | 435/6.11 |
| 6,333,177 | B1 | * | 12/2001 | Brukner et al.   | 435/91.1 |
| 2004/0197793 | A1 | * | 10/2004 | Hassibi et al. | 435/6 |
| 2006/0194306 | A1 | * | 8/2006  | Herr et al.      | 435/287.2 |

* cited by examiner

*Primary Examiner* — Teresa E Strzelecka
*Assistant Examiner* — Suchira Pande
(74) *Attorney, Agent, or Firm* — Thomas C. Meyers; Brown Rudnick LLP (57) ABSTRACT

The present invention generally relates to methods for identifying nucleic acid ligands of a target molecule. In certain embodiments, the invention provides methods for identifying a nucleic acid ligand of a target molecule from a candidate mixture of nucleic acids, including contacting at least one target molecule with a candidate mixture of nucleic acids, in which the nucleic acids have different affinities for the target molecule, and separating in a single step nucleic acids that bind the target molecule with greatest affinity from nucleic acids that bind the target molecule with a lesser affinity and nucleic acids that do not bind the target molecule, thereby identifying the nucleic acid ligand of the target molecule.

7 Claims, 8 Drawing Sheets

| Well | Well Identifier | Peak ID | Melt Temp |
|---|---|---|---|
| A01 | oligo 1 HOH | A1.1 | 78.0 |
|  |  | A1.2 | 65.5 |
| A02 | oligo 1 0 (NBH) | No Peak |  |
| A03 | oligo 1 $10^{-6}$ | A3.1 | 73.5 |
| A04 | oligo 1 $10^{-5}$ | A4.1 | 74.0 |
| A05 | oligo 1 $10^{-4}$ | A5.1 | 74.0 |
| A06 | oligo 1 $10^{-3}$ | A6.1 | 73.0 |
| A07 | aptamers only | No Peak |  |
| B01 | oligo 2 HOH | B1.1 | 77.0 |
|  |  | B1.2 | 64.5 |
| B02 | oligo 2 0 (NBH) | No Peak |  |
| B03 | oligo 2 $10^{-6}$ | B3.1 | 78.0 |
| B04 | oligo 2 $10^{-5}$ | B4.1 | 78.5 |

METHODS FOR IDENTIFYING NUCLEIC ACID LIGANDS

RELATED APPLICATION

The present application is a continuation of U.S. nonprovisional application Ser. No. 12/611,436, filed Nov. 3, 2009, the content of which is incorporated by reference herein in its entirety.

FIELD OF THE INVENTION

The present invention generally relates to methods for identifying nucleic acid ligands of a target molecule.

BACKGROUND

A nucleic acid ligand (aptamer) is a nucleic acid macromolecule (e.g., DNA or RNA) that binds tightly to a specific molecular target. Like all nucleic acids, a particular nucleic acid ligand may be described by a linear sequence of nucleotides (A, U, T, C and G), typically 15-40 nucleotides long. In solution, the chain of nucleotides forms intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Nucleic acid ligands are generally discovered using an in vitro selection process referred to as SELEX (Systematic Evolution of Ligands by EXponential enrichment). See for example Gold et al. (U.S. Pat. No. 5,270,163). SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule.

While successful at eventually generating high affinity nucleic acid ligands, the SELEX process requires multiple time consuming rounds of selection, partitioning, and amplification, because during nucleic acid ligand selection, low affinity nucleic acid ligands are at an increased concentration in a nucleic acid ligand library compared to high affinity nucleic acid ligands. SELEX requires multiple rounds to isolate the high affinity nucleic acid ligands because the low affinity nucleic acid ligands must be eliminated gradually to ensure eventual selection of the high affinity nucleic acid ligands.

There is an unmet need for methods that can more efficiently discover nucleic acid ligands to target molecules.

SUMMARY

The present invention provides methods for rapid (e.g., single step) and direct isolation of nucleic acid ligands of high affinity to a target molecule. Methods of the invention accomplish single step identification of nucleic acid ligands by employing selective separation protocols (e.g., gel electrophoresis or HPLC gradient elution) that eliminate undesirable competition for the target molecule among nucleic acids that bind the target molecule with greatest affinity, nucleic acids that bind the target molecule with a lesser affinity, and nucleic acids that do not bind the target molecule. The selective separation protocols generate conditions in which the nucleic acids that bind the target molecule with a lesser affinity and nucleic acids that do not bind the target molecule cannot form complexes with the target molecule or can only form complexes with the target molecule for a short period of time. In contrast, the conditions of the separation protocols allow nucleic acids that bind the target molecule with greatest affinity to form complexes with the target molecule and/or bind the target molecule for the greatest period of time, thereby separating in a single step the nucleic acids with the greatest affinity for the target molecule, i.e., the nucleic acid ligands, from the remainder of a candidate mixture of nucleic acids.

An aspect of the invention provides methods for identifying a nucleic acid ligand of a target molecule from a candidate mixture of nucleic acids including contacting at least one target molecule with a candidate mixture of nucleic acids, in which the nucleic acids have different affinities for the target molecule, and separating in a single step nucleic acids that bind the target molecule with greatest affinity from nucleic acids that bind the target molecule with a lesser affinity and nucleic acids that do not bind the target molecule, thereby identifying the nucleic acid ligand of the target molecule. The target molecule can by any type of biomolecule or a complex of biomolecules. Exemplary target molecules include a cell, cellular fragment, protein or portion thereof, an enzyme, a peptide, an enzyme inhibitor, a hormone, a carbohydrate, a glycoprotein, a lipid, a phospholipid, and a nucleic acid. In a particular embodiment, the target molecule is an infectious prion.

Separating can be accomplished by any of numerous methods that provide for selective single step separation of nucleic acids that bind the target molecule with greatest affinity from nucleic acids that bind the target molecule with a lesser affinity and nucleic acids that do not bind the target molecule. In certain embodiments, separating includes loading the target molecule into a gradient gel, applying an electric current to cause the target molecule to migrate to a position in the gel, in which the target molecule remains immobilized at that position in the gel, loading the candidate mixture into the gel, and applying an electric current to cause the candidate mixture to migrate through the gel, in which the nucleic acids with the greatest affinity for the target molecule (i.e., nucleic acid ligands) bind to the target molecule immobilized in the gel, and the nucleic acids with lesser affinity for the target molecule and nucleic acids with no affinity for the target molecule migrate to an end of the gel. The nucleic acid ligand/target molecule complex is then cut from the gel, and the nucleic acid ligands are then dissociated from the target molecules using a chaotropic agent.

In other embodiments, separating includes incubating the candidate mixture of nucleic acids with a plurality of target molecules to form nucleic acid/target molecule complexes, in which the target molecules are bound to beads, and eluting the nucleic acids from the complexes that have been loaded onto an HPLC column by applying an HPLC gradient profile, in which nucleic acids with the greatest affinity for the target molecule elute at an end portion of the gradient profile and the nucleic acids with a lesser affinity for the target molecule and nucleic acids with no affinity for the target molecule elute prior to the end portion of the gradient profile. Many different HPLC gradient elution profiles are known in the art. An exemplary HPLC gradient elution profile may include a linear increasing concentration of the target molecule, in which an end portion of the gradient profile may include a linear increasing concentration of the target molecule and a chaotropic agent (e.g., urea, guanidinium chloride, $SCN^-$, or LiBr). Prior to incubating, the method may further include loading the target molecules bound to the beads into an HPLC column. Alternatively, subsequent to incubating, the method may further include loading the candidate mixture and the nucleic acid/target molecule complexes onto an HPLC column.

Methods of the invention may further include sequencing the nucleic acid ligand. Sequencing may be accomplished by any method known in the art. In a particular embodiment, sequencing is a single-molecule sequencing by synthesis technique. The nucleic acid ligand may include DNA or RNA.

Another aspect of the invention provides methods for identifying a nucleic acid ligand of a target molecule from a candidate mixture of nucleic acids including contacting a candidate mixture of nucleic acids to a target molecule under conditions to form a plurality of target/nucleic acid complexes, in which the nucleic acids have different affinities for the target molecule and the nucleic acids that form the complex are the nucleic acids that have an increased affinity for the target molecule compared to the remainder of the nucleic acids in the mixture, separating the target/nucleic acid complexes from the remainder of the mixture, and dissociating the complexes in a manner in which bound nucleic acids dissociate from the target molecules at different rates based upon the different affinities of the bound nucleic acids to the target molecule, in which nucleic acids that dissociate from the target molecule at slowest rate are identified as the nucleic acid ligands of the target molecule. The method can further include collecting the nucleic acid ligand.

tive symptoms can include convulsions, dementia, ataxia (balance and coordination dysfunction), and behavioral or personality changes.

The protein that prions are made of (PrP) is found throughout mammals, such as humans, sheep, cow, pigs, goats, etc. However, PrP found in infectious material has a different structure and is resistant to proteases, enzymes that normally break down proteins. The normal form of the protein is named $PrP^C$, while the infectious form is named $PrP^{Sc}$. $PrP^C$ is a normal protein found on the membranes of cells, having 209 amino acids (in humans), a disulfide bond, a molecular weight of 35-36 kDa, and a mainly α-helical structure. Several topological forms exist, one cell surface form anchored via glycolipid and two transmembrane forms. $PrP^C$ is readily digested by proteinase K and can be liberated from the cell surface in vitro by the enzyme phosphoinositide phospholipase C (PI-PLC), which cleaves the glycophosphatidylinositol (GPI) glycolipid anchor. $PrP^C$ may function in cell-cell adhesion of neural cells, and/or be involved in cell-cell signaling in the brain.

The infectious isoform of PrP, known as $PrP^{Sc}$, is able to convert normal $PrP^C$ proteins into the infectious isoform by changing the conformation, which alters the way the proteins interconnect. $PrP^{Sc}$ has a higher proportion of β-sheet structure in place of the normal α-helix structure. Aggregations of these abnormal isoforms form highly structured amyloid fibers, which accumulate to form plaques. The end of each fiber acts as a template onto which free protein molecules may attach, allowing the fiber to grow. Only PrP molecules with an identical amino acid sequence to the infectious $PrP^{Sc}$ are incorporated into the growing fiber.

Methods of the invention involve contacting at least one target molecule with a candidate mixture of nucleic acids, in which the nucleic acids have different affinities for the target molecule. The nucleic acid ligands in the candidate mixture have specific binding regions that are capable of forming complexes of the greatest affinity with an intended target molecule in a sample in which remaining nucleic acids in the candidate mixture either do not form a complex with the target molecule or form a complex with the target molecule with a lesser affinity than the nucleic acid ligands.

Specificity of binding is measured in terms of the comparative dissociation constants (Kd) of the nucleic acid ligands for target as compared to the dissociation constant with respect to the nucleic acid ligands and other nucleic acids in the candidate mixture. Typically, the Kd for the nucleic acid ligand with respect to the target molecule will be 2-fold, 5-fold, or 10-fold less than the Kd with respect to target and the remaining nucleic acids in the candidate mixture. In certain embodiments, the Kd will be 50-fold less, 100-fold less, or 200-fold less. The binding affinity of the nucleic acid ligands with respect to the target molecule is measured in terms of Kd. The value of this dissociation constant can be determined directly by well-known methods, and can be computed for complex mixtures by methods such as those shown in Caceci et al. (Byte, 9:340-362, 1984).

Methods of the invention further include separating in a single step nucleic acids that bind the target molecule with greatest affinity from nucleic acids that bind the target molecule with a lesser affinity and nucleic acids that do not bind the target molecule, thereby identifying the nucleic acid ligand of the target molecule. The selective separation protocols generate conditions in which the nucleic acids that bind the target molecule with a lesser affinity and nucleic acids that do not bind the target molecule cannot form complexes with the target molecule or can only form complexes with the target molecule for a short period of time. In contrast, the conditions of the separation protocols allow nucleic acids that bind the target molecule with greatest affinity to form complexes with the target molecule and/or bind the target molecule for the greatest period of time, thereby separating in a single step the nucleic acids with the greatest affinity for the target molecule, i.e., the nucleic acid ligands, from the remaining nucleic acids in the candidate mixture.

Separating can be accomplished by any of numerous methods that provide for selective single step separation of nucleic acids that bind the target molecule with greatest affinity from nucleic acids that bind the target molecule with a lesser affinity and nucleic acids that do not bind the target molecule. Exemplary separating procedures include HPLC gradient elution and gel electrophoresis.

Figure 1:
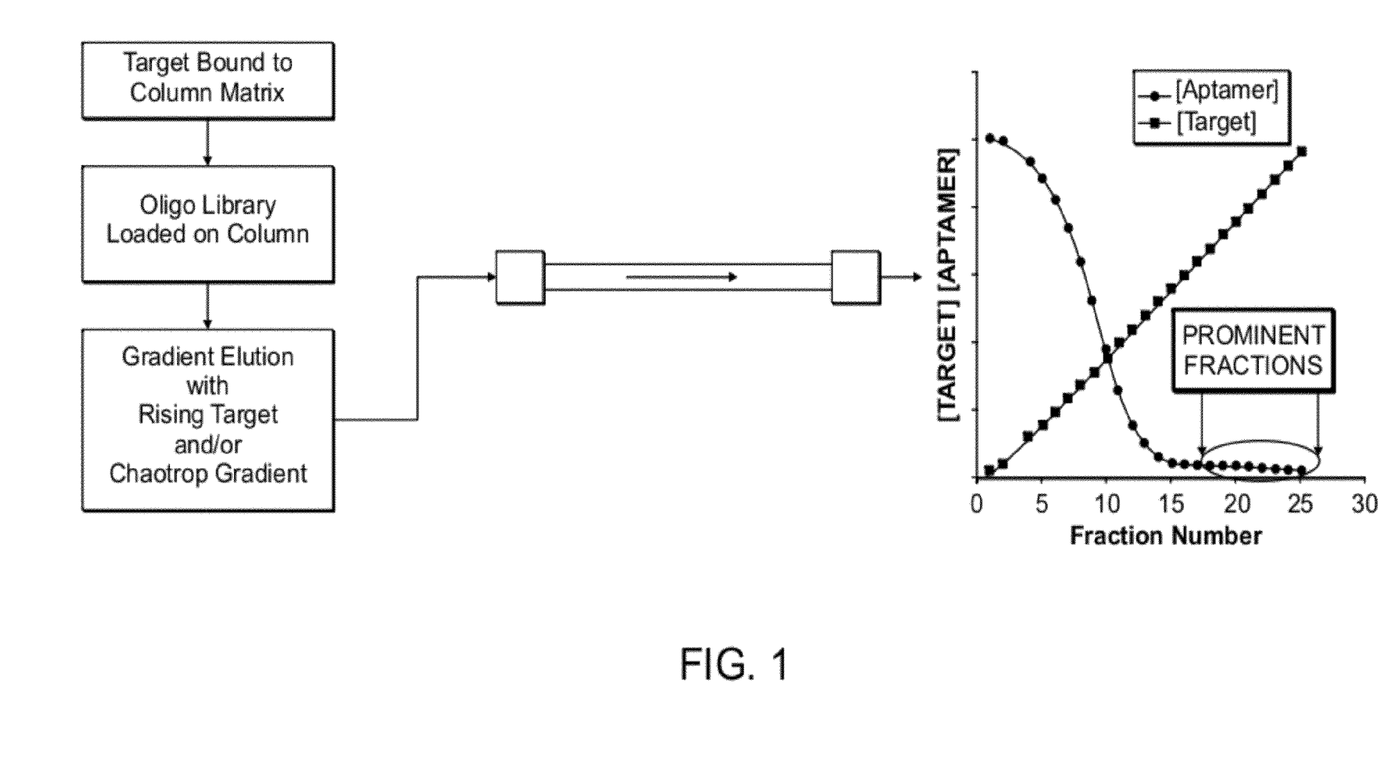
FIG. 1 provides a schematic diagram showing steps for a single step separation protocol using HPLC gradient elution from an HPLC column.

FIG. 1 is a schematic diagram showing steps for a single step separation protocol using HPLC gradient elution from an HPLC column. In this separation protocol, a competition of epitopes for nucleic acid ligands is generated such that at a certain ratio of target to nucleic acid ligand concentration, almost all nucleic acid ligands exhibiting apparent affinity to the target molecule are bound to the target, which is provided in excess of the nucleic acids in the candidate mixture. When binding is completed, the system is exposed to a flow of fresh solution of gradually decreasing target concentration. During gradual decrease of target concentration, different equilibriums (the equation for which is shown in Equation 1 below), for each given nucleic acid/target complex is achieved.

$$A+T \rightarrow AT$$

$$K^i_D = [A] \cdot [T] \cdot [AT]^{-1} \qquad \text{Equation 1}$$

where: A is an aptamer, T is a target molecule, AT is an aptamer/target molecule complex, and $K^i_D$ is the dissociation constant for a given aptamer/target molecule complex.

Because $K^i_D$ does not depend on concentrations of A, [A], and T, [T], and based on the law of mass action, gradual increase of [T] results in decrease of concentration of a given aptamer $[A_i]$. Thus, during the elution process the effluent will be enriched in aptamers of higher affinity to target, and eventually the final fractions contain the aptamers of the highest affinity to the target. It is envisioned that some sequences may show exceptionally high affinity to target and will not be apparently eluted even when the target in the solution reaches its maximum. To obtain those very selective structures the end of the elution process may include increasing concentration of a chaotropic agent, such as urea, guanidinium chloride, $SCN^-$, or LiBr. Thus the fractions of the highest affinity aptamers will be eluted gradually.

FIG. 1 shows that beads are saturated with target molecule. The beads can be any beads suitable for use during HPLC protocols. Numerous types of beads are known in the art and are commercially available, for example, from Sigma-Aldrich (St. Louis, Mo.). The beads can be porous beads or nonporous beads. FIG. 1 shows the beads as nonporous beads. The beads are activated using procedures known in the art and then incubated with target molecule, thereby allowing the target molecules to bind to the beads. An exemplary protocol for activating HPLC beads and binding target molecules to the beads in shown in Example 1 below. Incubation times can be easily determined by one of skill in the art. Factors that influence incubation time include type of target molecule, type of bead, strength of the binding interaction, and levels of any nonspecific binding. Incubation can be for as short at 1 min. or can be for greater than 24 hrs. In certain embodiments, incubation overnight.

After incubation, the mixture is washed with buffer to remove unbound target molecules. The beads having bound target molecules are then incubated with the candidate mixture of nucleic acids. The beads having bound target molecules can be loaded into an HPLC column prior to incubating with the candidate mixture. If the beads having bound target molecules are loaded into the HPLC column prior to incubation with the candidate mixture, incubating of the candidate mixture and the target molecule occurs on the column.

Alternatively, the beads having bound target molecule can be incubated with the candidate mixture and then the mixture of bead/target molecule/nucleic acid complexes and remainder of the candidate mixture can be loaded into the HPLC column. FIG. 1 shows incubation of the candidate mixture with the beads having bound target molecules prior to loading into the HPLC column. After incubation is complete, the bead/target molecule/nucleic acid complexes and remainder of the candidate mixture are loaded into the HPLC column. Incubation times can be easily determined by one of skill in the art. Factors that influence incubation time include type of target molecule, the make-up of the candidate mixture, strength of the binding interaction, and levels of any nonspecific binding. Incubation can be for as short at 1 min. or can be for greater than 24 hrs. In certain embodiments, incubation occurs overnight.

After the candidate mixture has been incubated with the target molecules bound to the beads for sufficient time that bead/target molecule/nucleic acid complexes can form, an HPLC elution gradient is applied to the column in order to obtain the nucleic acid ligands of the target molecule. During the elution process the effluent will be enriched in nucleic acid ligands of higher affinity for the target molecule, and eventually the final fractions contain the nucleic acid ligands of the highest affinity to the target molecule (FIG. 1).

The gradient profile typically includes a linearly increasing concentration of target molecule. The gradient profile also includes an end portion. In certain embodiments, the end portion includes a linearly increasing concentration of target molecule. In other embodiments, the end portion includes a linearly increasing concentration of target molecule and a chaotropic agent. The unbound nucleic acids and the nucleic acids that have some affinity for the target molecule will elute from the column prior to the end portion of the gradient (FIG. 1). In certain embodiments, the unbound nucleic acid will elute at a beginning portion of the gradient and the nucleic acids that have some affinity for the target molecule will elute at a middle portion of the gradient.

The nucleic acids with greatest affinity for the target molecule require a high concentration of target molecule in the effluent to elute from the column. The nucleic acids with the greatest affinity for the target molecule elute at the end portion of the gradient profile, when the concentration of target molecule in the effluent is the highest (FIG. 1). These nucleic acids of the candidate mixture are identified as the nucleic acid ligands of the target molecule. In certain embodiments, some nucleic acids may show exceptionally high affinity to the target molecule and will not be eluted even when the target molecule in the effluent reaches its maximum. In this embodiment, those very selective structures are obtained at the end portion of the elution process using an increasing concentration of a chaotropic agent, such as urea, guanidinium chloride, $SCN^-$, or LiBr. Thus the fractions of the highest affinity nucleic acid ligands will be eluted gradually.

In other embodiments, the single step separation protocol involves native PAGE electrophoresis. In native PAGE, proteins are separated according to the net charge, size and shape of native structure of the protein. Electrophoretic migration occurs because most proteins carry a net negative charge in alkaline running buffers. The higher the negative charge density (more charges per molecule mass), the faster a protein will migrate. At the same time, the frictional force of the gel matrix creates a sieving effect, retarding the movement of proteins according to size and three-dimensional shape. Small proteins encounter only a small frictional force while large proteins encounter a larger frictional force. Thus native PAGE separates proteins based upon both charge and mass.

Because no denaturants are used in native PAGE, subunit interactions within a multimeric protein are generally retained and information can be gained about the quaternary structure. In addition, some proteins retain enzymatic activity following separation by native PAGE. Thus, it may be used for preparation of purified, active proteins.

In this separation protocol, target molecules are loaded into lanes of a gradient gel. An electric current is applied, causing the target molecules to migrate to a position in the gel. The gradient gel prevents the target molecule from migrating to the end of the gel, instead, the target molecule is immobilized at a single position in the gel. Each lane of the gel may contain the same target molecule. Alternatively, each lane of the gel may contain a different target molecule.

Once the target molecule has been immobilized in the gel, the lanes of the gel are loaded with the candidate mixture of nucleic acids. Each lane of the gel may be loaded with the same candidate mixture. Alternatively, each lane of the gel may contain a different candidate mixture. The electric current is applied and the candidate mixture migrates through the gel, while the target molecule remains immobilized at its position in the gel. As the candidate mixture migrates to the position in the gel where the target molecule is immobilized, the nucleic acids of the candidate mixture interact with the target molecule. Only the nucleic acids having the highest affinity for the target molecule, i.e., the nucleic acids that can withstand effect of dilution by the running buffer and effect of the electrostatic field, remain bound to the target molecule. The remainder of the candidate mixture, i.e., nucleic acids that have a lesser affinity for the target molecule or nucleic acids that have no affinity for the target molecule, will not be able to withstand the forces being applied and will not be capable of remaining bound/binding the target molecule, thus migrating to an end of the gel.

The nucleic acids that remain bound to the target molecule are identified as the nucleic acid ligands of the target molecule. These nucleic acid ligand/target molecule complexes may be cut from the gel and application of a chaotropic agent may be used to dissociate the nucleic acid ligands from the target molecules.

The nucleic acid ligands that are obtained by methods of the invention may then be sequenced. Any sequencing method known in the art e.g., ensemble sequencing or single molecule sequencing, may be used. One conventional method to perform sequencing is by chain termination and gel separation, as described by Sanger et al., Proc Natl Acad Sci USA, 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. See, e.g., Drmanac, et al. (Nature Biotech., 16:54-58, 1998). The contents of each of reference is incorporated by reference herein in its entirety.

In certain embodiments, sequencing is performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions.

Incorporation of a dideoxynucleotide into the nascent, i.e., elongating, DNA strand terminates DNA strand extension, resulting in a nested set of DNA fragments of varying length. Newly synthesized and labeled DNA fragments are denatured, and separated by size using gel electrophoresis on a denaturing polyacrylamide-urea gel capable of resolving single-base differences in chain length. If each of the four DNA synthesis reactions was labeled with the same, monochromatic label (e.g., radioisotope), then they are separated in one of four individual, adjacent lanes in the gel, in which each lane in the gel is designated according to the dideoxynucleotide used in the respective reaction, i.e., gel lanes A, T, G, C. If four different labels were utilized, then the reactions can be combined in a single lane on the gel. DNA bands are then visualized by autoradiography or fluorescence, and the DNA sequence can be directly read from the X-ray film or gel image.

The terminal nucleotide base is identified according to the dideoxynucleotide that was added in the reaction resulting in that band or its corresponding direct label. The relative positions of the different bands in the gel are then used to read (from shortest to longest) the DNA sequence as indicated. The Sanger sequencing process can be automated using a DNA sequencer, such as those commercially available from PerkinElmer, Beckman Coulter, Life Technologies, and others.

In other embodiments, sequencing of the nucleic acid is accomplished by a single-molecule sequencing by synthesis technique. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Other single molecule sequencing techniques involve detection of pyrophosphate as it is cleaved from incorporation of a single nucleotide into a nascent strand of DNA, as is shown in Rothberg et al. (U.S. Pat. Nos. 7,335,762, 7,264,929, 7,244,559, and 7,211,390) and Leamon et al. (U.S. Pat. No. 7,323,305), the contents of each of which is incorporated by reference herein in its entirety.

If only a minimal amount of the nucleic acid ligand is obtained from the candidate mixture, PCR can be performed on the nucleic acid ligand in order to obtain a sufficient amount of nucleic acid ligand for sequencing (See e.g., Mullis et al. (U.S. Pat. Nos. 4,683,195, 4,683,202, and 4,800,159) and Saiki, R. K., et al., (Science, 239:487-491, 1988), the contents of each of which are incorporated by reference herein in its entirety).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Identifying Nucleic Acid Ligands Using an HPLC Gradient Elution Profile

Column Preparation

A SUPELCO ASCENTIS Si HPLC Column, 3 µm particle size, length×I.D. 3 cm×2.1 mm was obtained from Sigma-Aldrich (P No 581522-U). The column stationary phase was modified with aldehyde functionalities. The procedure involved:

Filling the column with 1% ethanol solution of 3-(trimethoxysilyl)butyl aldehyde (United Chemical Technologies, Bristol, Pa. PNo; PSX1050);

Incubation of the filled column for 30 min at room temperature;

Equilibration by 5 volumes of with absolute ethanol; and

Heating the column at 120° C. for 15 min.

The above procedure results in the formation of a thin coating of butyl aldehyde functionalities ready for protein attachment.

Binding of Target Molecule to Beads

The activated column was attached to a Waters HPLC system (Milford, Mass.), equilibrated with 50 mM PBS, pH 8.0. The target molecule, recombinant anthrax protective antigen (rPA), was applied to the coated surface via column filling with 0.5 mL containing 1 mg solution of rPA in the same buffer supplied with 4 mM sodium cyanoborohydride in five consecutive 0.1-mL injections. The Waters HPLC system consisted of Waters 600E controller and pump, Waters 717plus Autosampler and injector, and a Waters 996 Photodiode Array Detector. A FRAC-100 Fraction Collector (Pharmacia) was used to collect fractions containing nucleic acids.

After the overnight incubation, the column was extensively washed with fresh buffer to remove unbound protein, thus achieving a stable baseline ($A_{280}$<0.001). Binding of 46% of the applied rPA was confirmed. This amount of the protein, 460 µg, is equal to 5.55 nmol based on the rPA molecular weight of 83,000 Da.

The unreacted aldehyde surface groups were subsequently passivated by reaction with ethanolamine under similar conditions. The column was washed again with fresh 50 mM PBS, pH 8.0 and used for separation of DNA random 70 mers.

Preparation of Candidate Mixture

A 95.6 nmol batch of random 70 mer (Sigma-Genosys, Woodlands, Tex.) was reconstituted in 1 mL of 50 mM PBS, pH 8.0. Based on oligomer concentration, a 58-µL aliquot of this solution would contain 5.55 nmol of the oligonucleotides, which would be necessary to react in the equimolar ratio to the rPA protein bound within the column.

Nucleic Acid Ligand Capture

Narrow I.D. polypropylene tubing was connected directly to the HPLC pump and immersed into the oligomer solution. This solution was applied at a 0.2 mL/min flow rate directly on the silica HPLC column having the rPA and pre-equilibrated with 50 mM PBS, pH 8.0. The intake process was visually monitored. The flow rate was stopped when the last portions of the DNA oligomer solution reached the pump intake valve. Based on the geometrical estimation of the column void volume as being 52 µL (~50% porosity) by this procedure the column was filled with the amount of oligomers that was close to 5.55 nmol, or equimolar to the amount of rPA.

The column was left in the HPLC system to achieve nucleic acid ligand binding to the potential target molecule, rPA, on the surface of stationary phase. After 3 hrs, the 0.2 mL/min flow of the 50 mM PBS, pH 8.0 was resumed. The wash was continued until the absorbance at 260 nm reached less than 0.001 values.

Nucleic Acid Ligand Elution

The nucleic acid ligand elution was performed in one step using a gradient profile. The gradient profile involved an increasing gradient of the rPA concentration in the mobile phase. The end portion of the gradient profile involved an increasing gradient of the rPA concentration and an increasing gradient of a chaotropic agent, sodium thiocyanate (NaSCN). In order to reduce the total amounts of the required rPA, a direct HPLC pump feed method was used. A syringe pump was used to generate the gradient of the eluent concentration by continuously delivering a concentrated solution of rPA and/or NaSCN into a vial shaken on a vortex and containing measured amount of the equilibration buffer. The mixed eluent was applied on the column at 0.2 mL/min rate by the HPLC pump connected directly to the mixing vial. The 0.1 mL fractions were collected and dialyzed against di-water in 1250 Da cut off tubing to remove buffer salts. The dialysis step was important to remove NaSCN capable of absorbing UV light at 260 nm.

Figure 2:
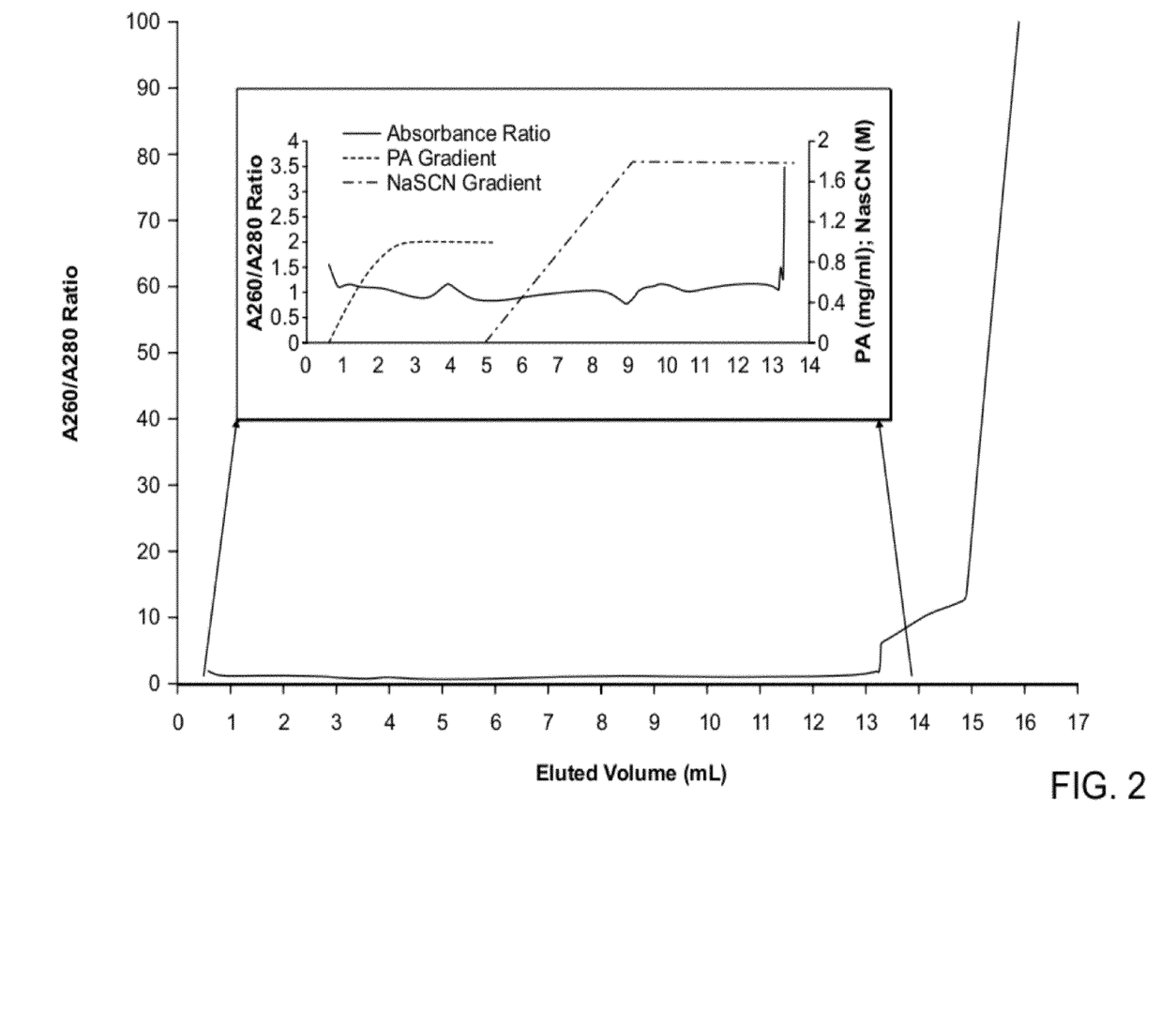
FIG. 2 is a graph showing a ratio of $A_{260}/A_{280}$ during nucleic acid ligand elution from an HPLC column as a function of eluted volume.

In order to confirm the elution of DNA oligonucleotides from the column, the $A_{260}$ and $A_{280}$ UV absorbance of the fractions were used. FIG. 2 depicts the ratio of $A_{260}/A_{280}$ as a function of the eluted volume. As long as the $A_{260}/A_{280}$ ratio for the DNA oligomers greatly exceeds 1.00 and the same ratio for the proteins is smaller than 1, this parameter allows detecting fractions enriched with the DNA oligomers. The UV spectra of the random 70 mer and rPA are shown in FIG. 2.

Figure 3:
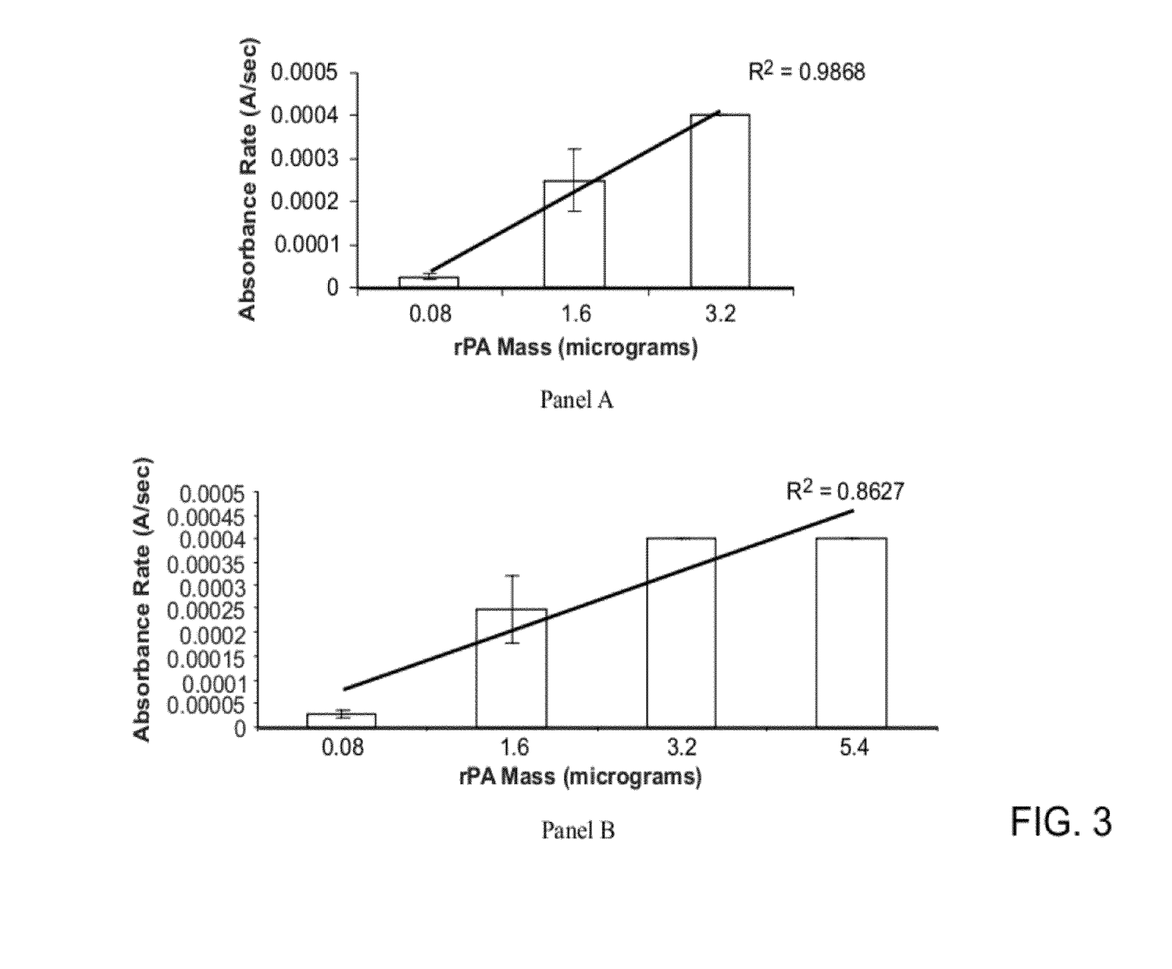
FIG. 3 panels A and B are graphs showing absorbance rates as a function of the rPA amount. Panel A is 0.08 to 3.2 μg rPA per well. Panel B is 0.08 to 5.4 μg rPA per well.

The data show that the ratio varied from 0.8 to 1.6 during the gradient profile. A substantial number of fractions showed ratios of more than 1.00 (highest was equal to 1.57 and eluted at 13.0 to 13.5 mL). While fractions obtained during elution with the rPA gradient contained protein and showed the maximum $A_{260}/A_{280}$ of 1.20, the fractions eluted with NaSCN were absorbing more intensively at 260 NM than at 280 nm, and the 13.0 to 13.5 mL fraction had the ratio equal to that of the used DNA oligomers (FIG. 3).

Nucleic Acid Ligand Identification and Affinity

Following the above described procedure a nucleic acid ligand was isolated from the last HPLC fraction. The nucleic acid ligand was sequenced at Sequagen Inc. (Worchester, Mass.), the sequence of which is provided below:

(SEQ ID NO: 1)
TACGACTCACTATAGGGATCCCGAGCTGCAATGGAGTGATTACTAGGGA

TGTGCGAGGCGCCGAATTCCCTTTAGTGAGGGTT.

This nucleic acid ligand showed an affinity to rPA of at least pM levels.

The affinity of this structure to rPA was estimated based on quantification of rPA detected by the biotinilated nucleic acid ligand during an ELISA process in a 96-well micro-titer plate format. More specifically, the ALISA (Aptamer-Linked Immobilized Sorbent Assay) procedure described in Vivekananda et al. (Lab Invest. 86(6):610-618, 2006) was adapted. The procedure included the following main steps:

The serial dilutions of rPA stock solution were used to coat the micro-titer plate wells in a concentration of 0.08 to 5.4 µg (approximately 1.0 to 68 pmol, assuming rPA MW of ~80,000 g/mol) per well.

After exposure, the non-specific binding sites were blocked with BSA solution.

The biotinilated nucleic acid ligand (synthesized at Sigma Genosys) solution was added (16 pmol/well). The nucleic acid ligand/biotin conjugate had the following structure:

(SEQ ID NO: 2)
[Btn]TACGACTCACTATAGGGATCCCGAGCTGCAATGGAGTGATTACT

AGGGATGTGCGAGGCGCCGAATTCCCTTTAGTGAGGGTT

After exposure the wells were washed and supplied with the solutions of polymerized streptavidin-HRP conjugates (Sigma Aldrich), washed again and supplied with hydrogen peroxide solution of the ABTS substrate.

The rPA was eventually determined using readings of OD rate at 405 nm during 10 to 30 min of the color development reaction.

The absorbance rates were measured and graphed. The blank absorbance rates (control, no rPA) was subtracted from the absorbance of the corresponding well contained rPA. The sequential repeats were performed to confirm the consistency of the acquired data. The absorbance rate as a function of the rPA amount is depicted in FIG. 3 panels A and B. Data herein confirm the affinity of the nucleic acid ligand isolated by methods of the invention to rPA of at least pM levels.

Example 2

Identifying Nucleic Acid Ligands Using Gel Electrophoresis

Preparation of Candidate Mixture

DNA oligomers were obtained from a well established library of PCR amplifiable DNA randomers described in Vivekananda et al. (Lab Invest. 86(6):610-618, 2006). This library was custom manufactured at Sigma-Genosys (The Woodlands, Tex.).

Nucleic Acid Ligand Capture

A solution containing infectious prion protein that resulted in chronic waste disease ($PrP^{CWD}$) was loaded into each well of a gradient gel. Native PAGE electrophoresis was performed to immobilize the infectious prion at a position in the gel. After immobilization of the infectious prion at a position in the gel, the concentrated solution of DNA randomers was loaded into each well of the gel. Electrophoresis was performed for a second time so that the DNA randomers would migrate through the gel already having the infectious prions immobilized at a position in the gel. Per each well, 25 μL of the prion protein solution and 25 μL of DNA oligomer solution containing 3.9 μg DNA were sequentially applied and electrophoretically resolved.

During the second electrophoretic step, the $PrP^{CWD}$ proteins barely moved in the electrophoretic field and stayed trapped in the network of the gradient gel, while the small DNA oligomers (MW of 21 kDa) were able to migrate towards the positive electrode. Only those DNA oligomers that showed high affinity to $PrP^{CWD}$ and could withstand the effect of dilution by the running buffer and the effect of the electrostatic field remained attached to the target protein. Remaining DNA randomers migrated past the $PrP^{CWD}$ to an end of the gel.

Figure 4A:
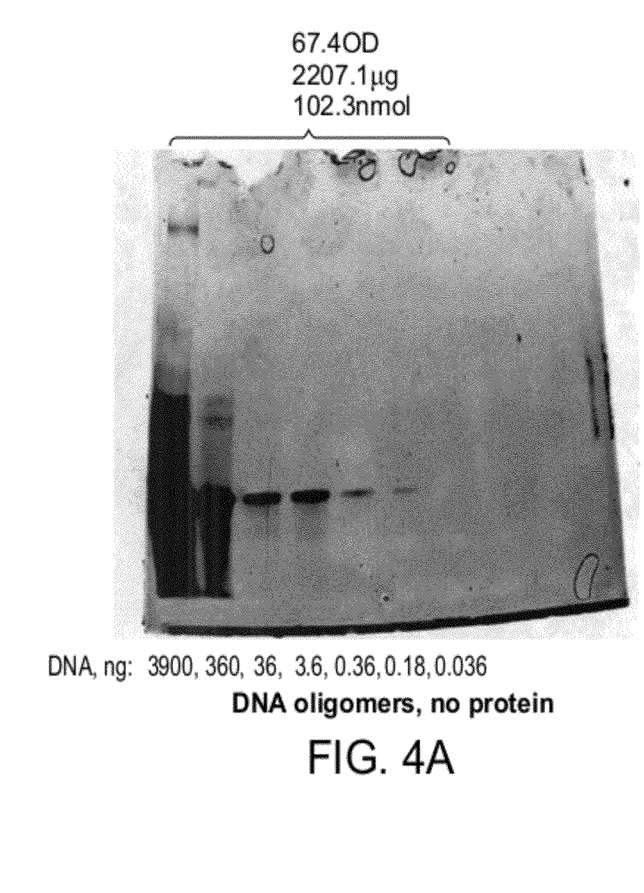
FIG. 4 panels A and B are photographs of a gel containing isolated nucleic acid ligands bound to infectious prions. Panel A shows a DNA titration gel showing band density as function of DNA oligomer concentration. Panel B shows a gel obtained by sequential application and electrophoresis of protein and DNA randomer solutions. The area of $PrP^{Sc}$ protein stained with EB due to presence of DNA is circled.
Figure 4B:
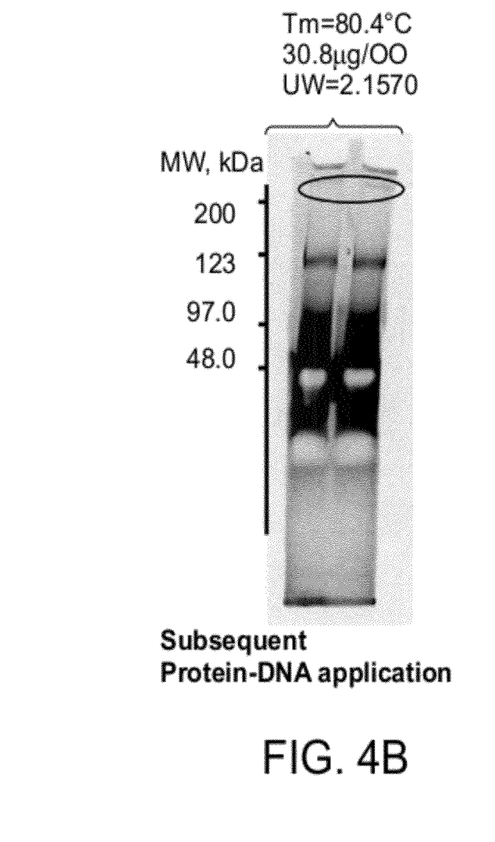

After the second electrophoretic step, the gels were stained with Ethidium Bromide (EB) to detect and quantify DNA oligomer bound to the $PrP^{CWD}$ protein within the gel. After performing the above procedure retention of some small quantities of DNA oligonucleotides located on the $PrP^{CWD}$ entrapped in the gel was observed (FIG. 4). Panel A of FIG. 4 is a control showing an electrophoresis run of only DNA randomers, no protein. Panel B shows gels obtained by sequential application and electrophoresis of protein and DNA randomer solutions. The area of DNA randomer/ $PrP^{CWD}$ complexes stained with EB due to presence of DNA is circled.

Figure 5:
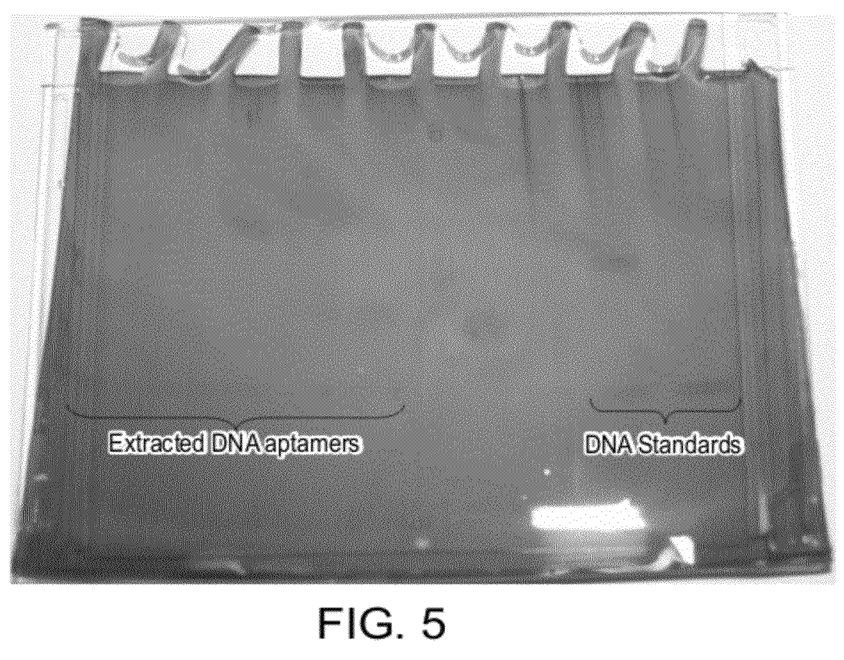

As shown in FIG. 4 panel B, sub ng quantities of DNA were observed in the area of localization of DNA randomers complexed with $PrP_{CWD}$ protein. This allowed collection and amplification/sequencing of this DNA fraction as a potential candidate for $PrP^{CWD}$ detection. The estimate of the affinity of the retained aptamer was provided using the estimated amounts of $PrP^{CWD}$ (~400 ng, FIG. 4) and nucleic acid ligand (~0.18 ng, FIG. 5), and average molecular weight of the $PrP^{CWD}$ protein of 275×10³ g/mol. Thus, the dissociation constant was determined by Equation 2.

$$K_d = [PrP^{CWD}] \times [Apt]/[PrP^{CWD}Apt]/MWPr^{CWD}\text{protein} \quad \text{Equation 2}$$

where: $[PrP^{CWD}]$ is the equilibrium quantity of the prion protein (ng); [Apt] is the equilibrium quantity of the retained aptamer (ng); $[PrP^{CWD}Apt]$ is the is the equilibrium quantity of the complex of the prion protein and retained aptamer (ng); and $MWPrP^{CWD}$ protein is the molecular weight of the detected $MWPrP^{CWD}$ protein ng/nmol.

$$K_d = 400 \times 0.18/418/(275 \times 10^3);$$

$$K_d = 6 \times 10^{-5} \text{ nmol}$$

Nucleic Acid Ligand Isolation

In order to obtain protein free aptamers via PAGE, the zones containing nucleic acid ligands bound to $PrP^{CWD}$ were carefully cut from the polyacrylamide gels and treated with chaotropic agent (2.0 M solution of sodium thiocyanate, NaSCN). A total of three 1×8 cm gel fragments were immersed in 10 mL of the NaSCN solution in a 50 mL Falcon tube and vortexed for 1 hr at ~1000 rpm. The resultant gel-water suspension was filtered through a 0.8 micron cellulose acetate syringe filter. The filtrate was analyzed for the presence of DNA aptamers by PAGE (4-20% gradient gel) with silver staining according to the protocol provided by BioRad Laboratories. DNA 70-randomer was used to serve as standards for this run. As seen in FIG. 5, the DNA nucleic acid ligands were diluted given the faint bands appearing in the gel.

Nucleic Acid Ligand Amplification

The nucleic acid ligands were amplified by PCR in a G-storm thermal cycler at IST. More specifically, PCR amplification was performed by adding the collected nucleic acid ligands, primers, and nuclease free water to the EconoTaq 2× Master Mix (Table 1) and following amplification steps depicted in Table 2.

TABLE 1

PCR reagent composition

| Reagent | Amount (μl) | Concentration | Final Concentration |
|---|---|---|---|
| Lucigen Econotaq 2X Master Mix | 25 | 2X | 1X |
| Primer AP7: TAC GAC TCA CTA TAG GGA TCC (SEQ ID NO: 3) | 1.0 | 50 pmol/μl | 1 pmol/μl |
| Primer AP3: AAC CCT CAC TAA AGG GAA TT (SEQ ID NO: 4) | 1.0 | 50 pmol/μl | 1 pmol/μl |
| Nucleic acid ligand: 5'-TAC GAC TCA CTA TAG GGA TCC- (N = 28) -GAA TTC CCT TTA GTG AGG GTT-3' (SEQ ID NO: 5) | 1.0 | ~1 ng/μl | <1 ng/μl |
| Nuclease Free Water | 22.0 | — | — |

TABLE 2

PCR steps

| Cycling step | Temperature (° C.) | Time | # of Cycles |
|---|---|---|---|
| Initial Denaturation | 95 | 2 min | 1 |
| Denaturation | 95 | 30 sec | 30 |
| Annealing* | 50-65 *52.9 | 30 sec | 30 |
| Extension | 72 | 30 sec | 30 |
| Final Extension | 72 | 5 min | 1 |
| Hold | 4 | overnight | 1 |

*Optimum annealing temperature

Figure 6:
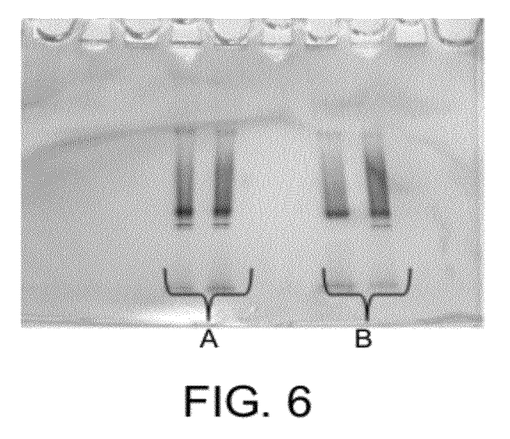

In this manner 4.0 mL solution containing 100 µg of >80% pure nucleic acid ligands was generated (FIG. 6, Lane B).

Nucleic Acid Ligand Identification

The PCR amplification provided amplified material that was sequenced at Sequegen Inc, Worcester, Mass. The obtained nucleic acid ligand sequences were used to generate micromole quantities of the purified nucleic acid ligand sequences at Sigma-Genosys (The Woodlands, Tex.). The sequences of the obtained nucleic acid ligands were as follows:

(SEQ ID NO: 6)
TACGACTCACTATAGGGATCCGTTTTTCCGTACTTCTTAAATCGAATTC

CCTTTAGTGAGGGTT;

(SEQ ID NO: 7)
TACGACTCACTATAGGGATCCTTCTCCGCACTACTTTACCTCGAGTGCT

ATTCCCTTTAGTGAGGGTT.

Nucleic Acid Ligand Affinity and Specificity Assay

Figure 7:
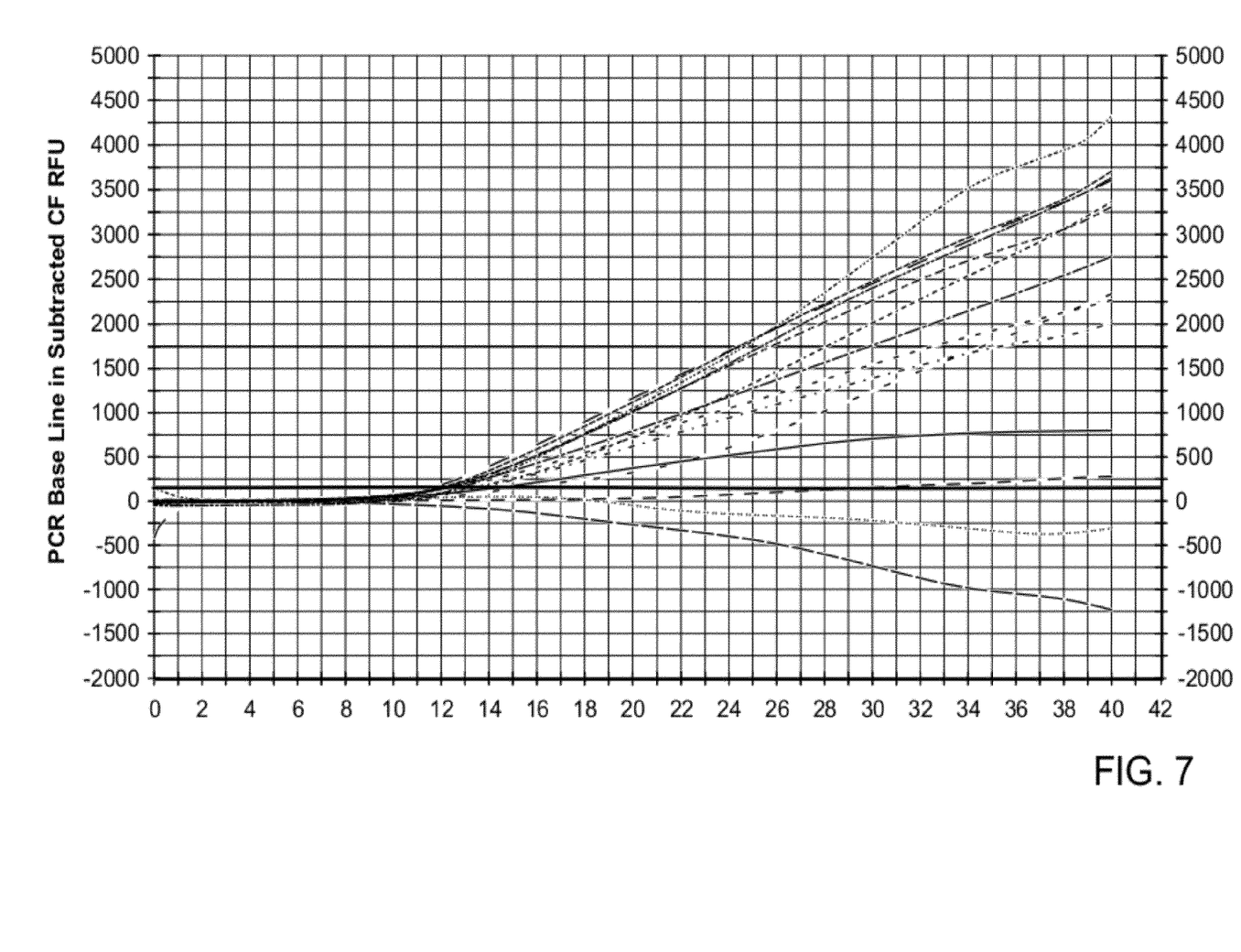

To evaluate the specificity of the generated DNA nucleic acid ligands, quantitative real-time PCR (qrt-PCR) was used to quantify low amounts of bound nucleic acid ligand from $PrP^{CWD}$ positive biological samples. The following process was used:

1. Diluted the elk strain of CWD prions (designated as E2) used in the nucleic acid ligand isolation protocol in PBS from 1:10 to 1:100,000.
2. 1:10 dilutions of uninfected normal brain homogenate (NBH) were used as negative controls.

3. 20 μL of each dilution sample was incubated with 180 μL of 1 μM of two different nucleic acid ligand (SEQ ID NO: 6 and SEQ ID NO: 7) for twenty minutes at room temperature.

4. Unbound nucleic acid ligands were removed from the samples by dilution with 300 μL PBS and filtration through a 100 Kd spin column.

5. Step 4 was repeated twice, substituting 500 μL 500 mM NaSCN for PBS.

6. Samples were concentrated to fifty microliters, and nucleic acid ligands purified using the DNeasy blood and tissue kit (Qiagen).

7. Nucleic acid ligands were eluted from columns with 50 μL Tris-EDTA buffer and ten microliters used for nucleic acid ligand detection by real-time PCR using primers specific for nucleic acid ligands and SYBR Green fluorescent DNA-intercalating dye.

8. Two HOH-only samples were used as negative controls for PCR.

9. All samples were incubated for one pre-melt cycle for three minutes at 95° C., then thirty cycles of twenty seconds at 95° C. and 45 seconds at 50° C. for annealing and extension and a final cycle for five minutes at 50° C.

After forty PCR cycles, both negative HOH controls (cyan and green traces (FIG. 7) and Table 3) remained below fluorescent detection threshold (orange horizontal line). The 1:10 E2 dilutions were off the scale where the fluorescence signal was detected without the need for amplification ($C_T$=0). All other E2 dilutions were detected with $C_T$ values of 11.7 for 1:100 to 20.3 for 1:100 000 dilutions. Background detection of nucleic acid ligands eluting with the NBH dilutions (red and blue traces, FIG. 7) was easily distinguished from all other samples, which were well above 1000 relative fluorescence units. Table 3 summarizes the results shown in FIG. 7.

TABLE 3

| $C_T$ values for RT-PCR samples | | |
|---|---|---|
| Well | Identifier | Ct |
| A01 | HOH | N/A |
| A02 | HOH | N/A |
| B01 | 1:10 E2 (SEQ ID NO: 6) | 0 |
| B02 | 1:10 E2 (SEQ ID NO: 7) | 0 |
| C01 | 1:100 E2 (SEQ ID NO: 6) | 11.7 |
| C02 | 1:100 E2 (SEQ ID NO: 7) | 11.4 |
| D01 | 1:1000 E2 (SEQ ID NO: 6) | 11.4 |
| D02 | 1:1000 E2 (SEQ ID NO: 7) | 12.3 |
| E01 | 1:10,000 E2 (SEQ ID NO: 6) | 13.3 |
| E02 | 1:10,000 E2 (SEQ ID NO: 7) | 15.7 |
| F01 | 1:100,000 E2 (SEQ ID NO: 6) | 20.3 |
| F02 | 1:100,000 E2 (SEQ ID NO: 7) | 16.4 |
| G01 | 1:10 NBH (SEQ ID NO: 6) | 17.4 |
| G02 | 1:10 NBH (SEQ ID NO: 7) | 28.4 |

In Table 3, the $C_T$ values represented the number of cycles required for the fluorescence signal to cross the set threshold. A $C_T$ value≦29 indicated an abundance of the target, a $C_T$ value of 30-37 indicated a positive detection of the target, and a $C_T$ value of 38-40 indicated the presence of a weak or small amount of the target.

This data show that the two nucleic acid ligands identified by methods of the invention successfully detected up to a 100,000-fold dilution of E2 CWD prions. This detection threshold is at least 100-fold greater than detection by conventional western blotting. Further advances in optimization of the assay to achieve a detection limit to 1,000,000 dilutions of the prion sample are described below.

To simulate the real low pg and fg concentrations of infectious prions in bodily fluids, the affinity of the DNA nucleic acid ligands was further evaluated at 1:100,000 dilutions of brain homogenate (actual working dilution of $1.25\times10^6$ under the established PCR protocol). This dilution level represents a target sample concentration 0.3 pg/mL of $PrP^{Sc}$ in the tested brain homogenate which is well within the range of infectious prion levels found in the blood of live animals (Brown et al., J Lab Clin Med, 137(1):5-13, 2001). Therefore, this sensitivity provides for tests to be conducted on bio-fluids collected from live animals. For example, the concentration of the infectious prions in the blood of infected animals can be estimated at sub pg/mL levels, while the threshold of sensitivity for the detection of infectious prions extracted from scrapie-infected hamster brain has been estimated at 5 pg/mL (Brown et al., J Lab Clin Med, 137(1):5-13, 2001). The estimated concentration of $PrP^{Sc}$ in the urine of infected test animals has been estimated in the fg/mL (0.001 pg) levels (Gonzalez-Romero et al., FEBS Lett, 582(21-22):3161-3166, 2008). Therefore, the DNA nucleic acid ligands developed above can be used to detect infectious prions in about 10 μL of blood or 1 mL of urine.

Data obtained at the 1,000,000 dilutions showed that the infectious prions were detected (total $1.25\times10^6$ dilution) of the tested specimen. This corresponds to significant improvement of the detection limit to 0.025 pg/mL or 250 atto-grams in a 10 μL sample.

The detection of infectious prions in the 1:100,000 dilutions ($C_T$ of 16.4-20.3) are comparable to the low-level detection of nucleic acid ligands in the NBH samples (blue and red traces, $C_T$ of 17.4-28.4) which were at 1:10 dilutions. In addition, the relative fluorescent signals of the NBH samples were much lower and easily distinguishable from test samples (see FIG. 7). These data also showed that optimization removes the low-level detection of the NBH sample altogether. The fluorescence signal of the NBH samples at 1:100 dilutions would be extremely weak to non-existent.

Figure 8:
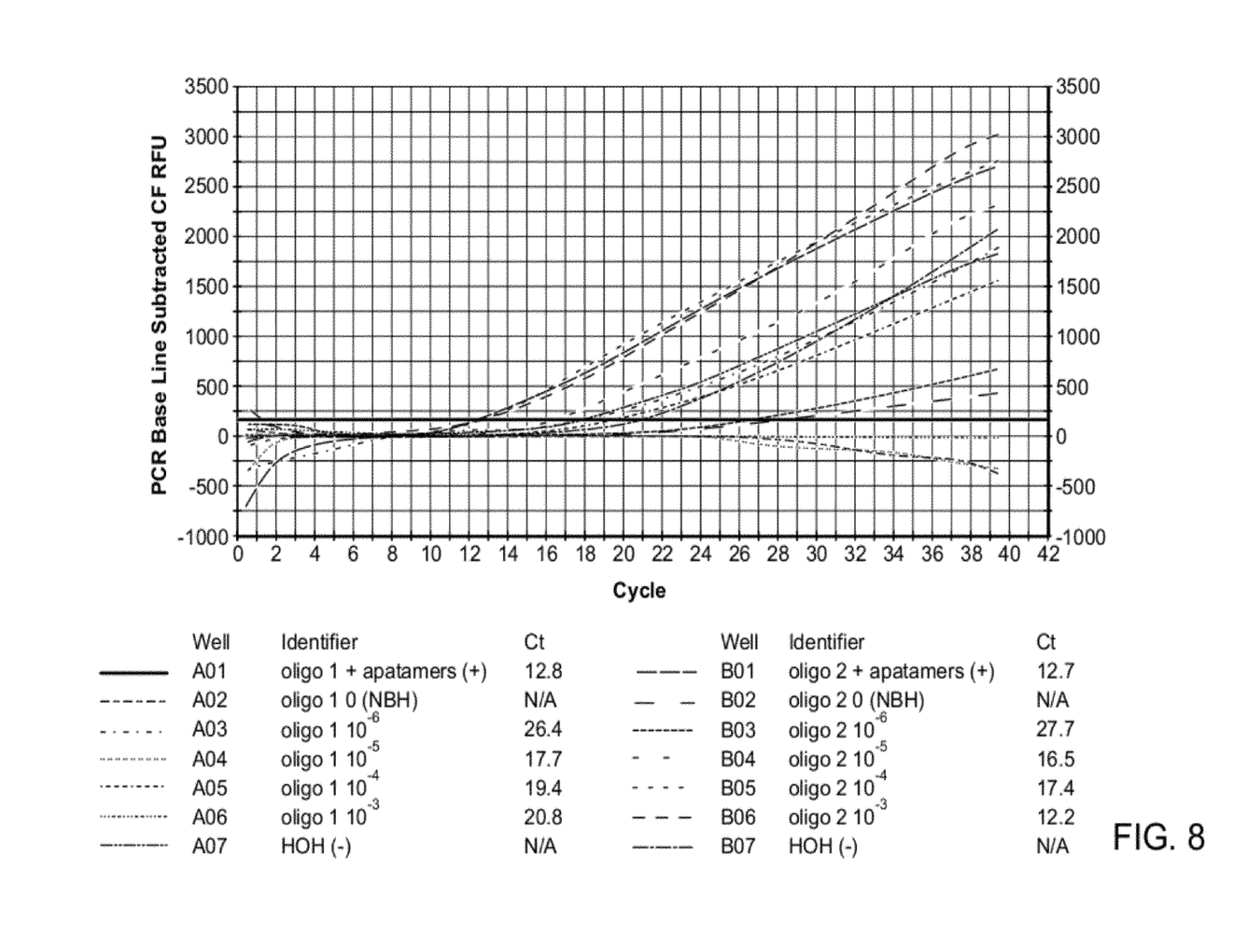

To completely eliminate background nucleic acid ligand noise in the samples, the samples were further treated with ten units of DNAse I for one minute to remove unbound nucleic acid ligands, while $PrP^{CWD}$-bound nucleic acid ligands were protected from digestion. Samples were then treated with 50 µg/mL proteinase K (PK) to eliminate DNAse I activity, then heat inactivated PK for ten minutes at 95° C. to maintain integrity and activity of the Taq polymerase used in the RT-PCR amplification of bound nucleic acid ligands. This DNAse I/PK/heat inactivation protocol completely eliminated possible background amplification of nucleic acid ligands in our negative control samples (FIG. 8) and obviated the need not only for NaSCN treatment and filtration, but also for nucleic acid ligand purification using the DNEasy tissue kit. The DNAse I and PK treatment greatly decreased the organic complexity of the samples, which could be used directly in the QRT-PCR reaction without the time and expense of further DNA extraction. The entire assay was completed from nucleic acid ligand incubation to RT-PCR to data analysis, in less than three hours. CWD prions were successfully detected in a $10^{-6}$ dilution of brain homogenate from a CWD-infected elk, corresponding to a thousand-fold increase in sensitivity over conventional proteinase K digestion/western blotting. Data also show prion detection in archived spleen tissue from mice infected with CWD (Table 4).

TABLE 4

Summary of additional data generated from subsequent binding assays

| Sample | Prion[1] | Dilution[2] | Detection[3] |
|---|---|---|---|
| Brain | Spiked | $10^{-2}$ | + |
| Brain | Spiked | $10^{-3}$ | + |
| Brain | Spiked | $10^{-4}$ | + |
| Brain | Spiked | $10^{-5}$ | + |
| Brain | Spiked | $10^{-6}$ | + |
| Brain | Infected | $10^{-3}$ | + |
| Brain | Negative | $10^{-1}$ | − |
| Brain | Negative | $10^{-2}$ | − |
| Brain | Negative | $10^{-3}$ | − |
| Spleen | Infected | $10^{-1}$ | + |
| Spleen | Negative | $10^{-1}$ | − |

Figure 9A:
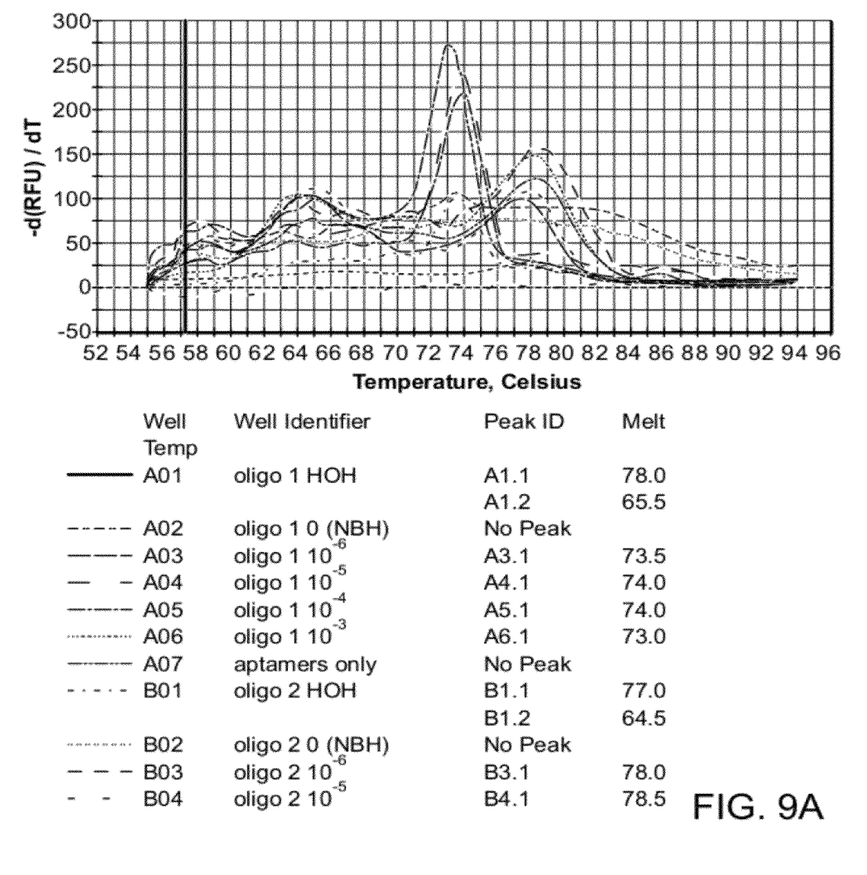
Figure 9B:
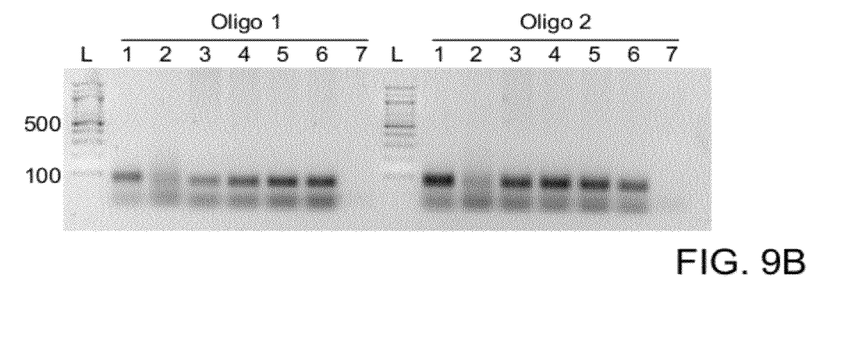

Generation of the specific nucleic acid ligand PCR products were confirmed by both melt curve analysis (FIG. 9 panel A) and agarose gel electrophoresis (FIG. 9 panel B) of amplified samples.

Data herein show that the selected DNA nucleic acid ligands generated by methods of the invention could detect infectious prions at levels as low as 0.03 pg/mL concentrations directly in 20 µL samples of biological specimens. This sensitivity is at least 1000-fold higher than what is achievable in immuno-enzymatic assays. Data herein further show the specificity of these DNA nucleic acid ligands for infectious prions over normal prions. There were no false positive or negative reactions in controls containing normal prion protein or no prion protein.

These results show that DNA nucleic acid ligands generated by methods of the invention can detect very low concentrations of infectious prion that are representative of concentrations found in biological fluids or samples such as blood, urine and feces.

What is claimed is:

1. A method for identifying a nucleic acid ligand of a target molecule from a candidate mixture of nucleic acids, the method comprising:
   loading at least one target molecule into a gradient gel;
   applying an electric current to cause the target molecule to migrate to a position in the gel, wherein the target molecule remains immobilized at that position in the gel;
   loading a candidate mixture of nucleic acids into the gel; and
   applying an electric current to cause the candidate mixture to migrate through the gel, wherein the nucleic acids with the greatest affinity for the target molecule bind to the target molecule immobilized in the gel, and the nucleic acids with lesser affinity for the target molecule and nucleic acids with no affinity for the target molecule migrate to an end of the gel.

2. The method according to claim 1, further comprising dissociating the bound nucleic acids from the target molecules.

3. The method according to claim 1, further comprising sequencing the nucleic acid ligand.

4. The method according to claim 3, wherein sequencing is a single-molecule sequencing by synthesis technique.

5. The method according to claim 1, wherein the target molecule is selected from the group consisting of: a protein or portion thereof, an enzyme, a peptide, an enzyme inhibitor, a hormone, a carbohydrate, a glycoprotein, a lipid, a phospholipid, and a nucleic acid.

6. The method according to claim 5, wherein the protein is an infectious prion.

7. The method according to claim 1, wherein the nucleic acid ligand comprises DNA or RNA.

* * * * *

SEQUENCE LISTING

```
<160> NUMBER OF SEQ ID NOS: 7

<210> SEQ ID NO 1
<211> LENGTH: 83
<212> TYPE: DNA
<213> ORGANISM: Artificial Sequence
<220> FEATURE:
<223> OTHER INFORMATION: Nucleic acid ligand against recombinant anthrax
      protective antigen (rPA)

<400> SEQUENCE: 1
tacgactcac tatagggatc ccgagctgca atggagtgat tactagggat gtgcgaggcg      60
ccgaattccc tttagtgagg gtt                                             83

<210> SEQ ID NO 2
<211> LENGTH: 83
<212> TYPE: DNA
<213> ORGANISM: Artificial Sequence
<220> FEATURE:
<223> OTHER INFORMATION: Nucleic acid ligand against recombinant anthrax
      protein (rPA)

<400> SEQUENCE: 2
tacgactcac tatagggatc ccgagctgca atggagtgat tactagggat gtgcgaggcg      60
ccgaattccc tttagtgagg gtt                                             83
```

```
<210> SEQ ID NO 3
<211> LENGTH: 21
<212> TYPE: DNA
<213> ORGANISM: Artificial Sequence
<220> FEATURE:
<223> OTHER INFORMATION: Primer AP7

<400> SEQUENCE: 3
tacgactcac tagggatc c                                              21

<210> SEQ ID NO 4
<211> LENGTH: 20
<212> TYPE: DNA
<213> ORGANISM: Artificial Sequence
<220> FEATURE:
<223> OTHER INFORMATION: Primer AP3

<400> SEQUENCE: 4
aaccctcact aaagggaatt                                              20

<210> SEQ ID NO 5
<211> LENGTH: 70
<212> TYPE: DNA
<213> ORGANISM: Artificial Sequence
<220> FEATURE:
<223> OTHER INFORMATION: Nucleic acid ligand
<220> FEATURE:
<221> NAME/KEY: misc_feature
<223> OTHER INFORMATION: n = A, C, G, or T
<220> FEATURE:
<221> NAME/KEY: misc_feature
<222> LOCATION: (22)..(49)
<223> OTHER INFORMATION: n is a, c, g, or t

<400> SEQUENCE: 5
tacgactcac tagggatc cnnnnnnnnnn nnnnnnnnnn nnnnnnnnng aattccctttt   60 agtgagggtt                                                         70

<210> SEQ ID NO 6
<211> LENGTH: 64
<212> TYPE: DNA
<213> ORGANISM: Artificial Sequence
<220> FEATURE:
<223> OTHER INFORMATION: Nucleic acid ligand against infectious prions

<400> SEQUENCE: 6
tacgactcac tagggatc cgttttccg tacttcttaa atcgaattcc ctttagtgag     60
ggtt                                                               64

<210> SEQ ID NO 7
<211> LENGTH: 68
<212> TYPE: DNA
<213> ORGANISM: Artificial Sequence
<220> FEATURE:
<223> OTHER INFORMATION: Nucleic acid ligand against infectious prions

<400> SEQUENCE: 7
tacgactcac tagggatc cttctccgca ctactttacc tcgagtgcta ttcccttag     60 tgagggtt                                                           68
```